United States Patent
Kaufman et al.

(10) Patent No.: US 6,679,828 B2
(45) Date of Patent: Jan. 20, 2004

(54) MAGNETIC KEY CHAIN

(76) Inventors: Jonathan Joseph Kaufman, 112 Willow St., Apt. 1A, Brooklyn, NY (US) 11201; Gocha Chkadua, 4901 W. 120th St., Apt. #1, Hawthorne, CA (US) 90250

(*) Notice: Subject to any disclaimer, the term of this patent is extended or adjusted under 35 U.S.C. 154(b) by 0 days.

(21) Appl. No.: 10/150,228

(22) Filed: May 17, 2002

(65) Prior Publication Data

US 2002/0173692 A1 Nov. 21, 2002

Related U.S. Application Data

(60) Provisional application No. 60/292,140, filed on May 18, 2001.

(51) Int. Cl.$^7$ .......................... A61M 2/00; E05M 39/04; A44C 5/00; A44B 21/00
(52) U.S. Cl. .......................... 600/15; 70/456 R; 63/3; 24/303; 600/9
(58) Field of Search ................. 70/456 R, 68, 70/458, 457; 604/270; 600/9, 12, 15; 463/47.4; 224/183, 251, 901; 206/5, 38.1; 24/3.3, 116 R, 299, 598.2, 600.6; 2/144, 153, 155; 40/634, 633; D11/13, 93; 150/106; 383/11; 603/298, 315; 29/896.4, 896.41, 417

(56) References Cited

U.S. PATENT DOCUMENTS

| | | | |
|---|---|---|---|
| 1,042,918 A | * 10/1912 | Houck | 70/457 |
| 3,177,546 A | * 4/1965 | Bey | 24/303 |
| 3,682,216 A | * 8/1972 | Nelson | 150/106 |
| 4,095,587 A | * 6/1978 | Ishikawa | 600/15 |
| 4,752,072 A | * 6/1988 | Parsons | 463/47.4 |
| 4,932,230 A | * 6/1990 | Ishii et al. | 70/456 R |
| 4,940,250 A | 7/1990 | Corrado | |
| 4,979,625 A | 12/1990 | Johnson et al. | |
| 5,024,078 A | 6/1991 | Fenwick | |
| 5,323,554 A | * 6/1994 | MacDonald | 40/633 |
| 5,367,891 A | * 11/1994 | Furuyama | 63/29.2 |
| 5,388,439 A | 2/1995 | Miller | |
| 5,431,640 A | * 7/1995 | Gabriel | 604/270 |
| 5,572,887 A | * 11/1996 | Geswelli | 63/3 |
| D391,515 S | * 3/1998 | Kennedy | D11/13 |
| 5,782,107 A | * 7/1998 | Glanz | 63/3 |
| 5,782,743 A | * 7/1998 | Russell | 600/9 |
| 5,827,170 A | * 10/1998 | Gebran | 600/15 |
| 5,836,018 A | * 11/1998 | Lee | 2/144 |
| 5,887,448 A | * 3/1999 | Gilbert et al. | 63/1.16 |
| 5,989,178 A | * 11/1999 | Chiu | 600/15 |
| 6,243,929 B1 | * 6/2001 | Curwood | 24/598.2 |
| 6,260,749 B1 | * 7/2001 | Horovitz | 224/183 |
| 6,344,021 B1 | * 2/2002 | Juster et al. | 600/15 |
| 6,406,418 B1 | * 6/2002 | Getek | 600/15 |

* cited by examiner

*Primary Examiner*—Eric F. Winakur
*Assistant Examiner*—Nikita R Veniaminov
(74) *Attorney, Agent, or Firm*—Dykema Gossett PLLC

(57) ABSTRACT

A magnetic key chain which provides for the ability to attach itself to a magnetic material, such as the inner surface of a front door of a home or a refrigerator door. The magnetic key chain also allows for therapeutic treatment of an anatomical site in a living body. In another embodiment, magnetic jewelry is adapted for both ornamental and therapeutic use.

20 Claims, 5 Drawing Sheets

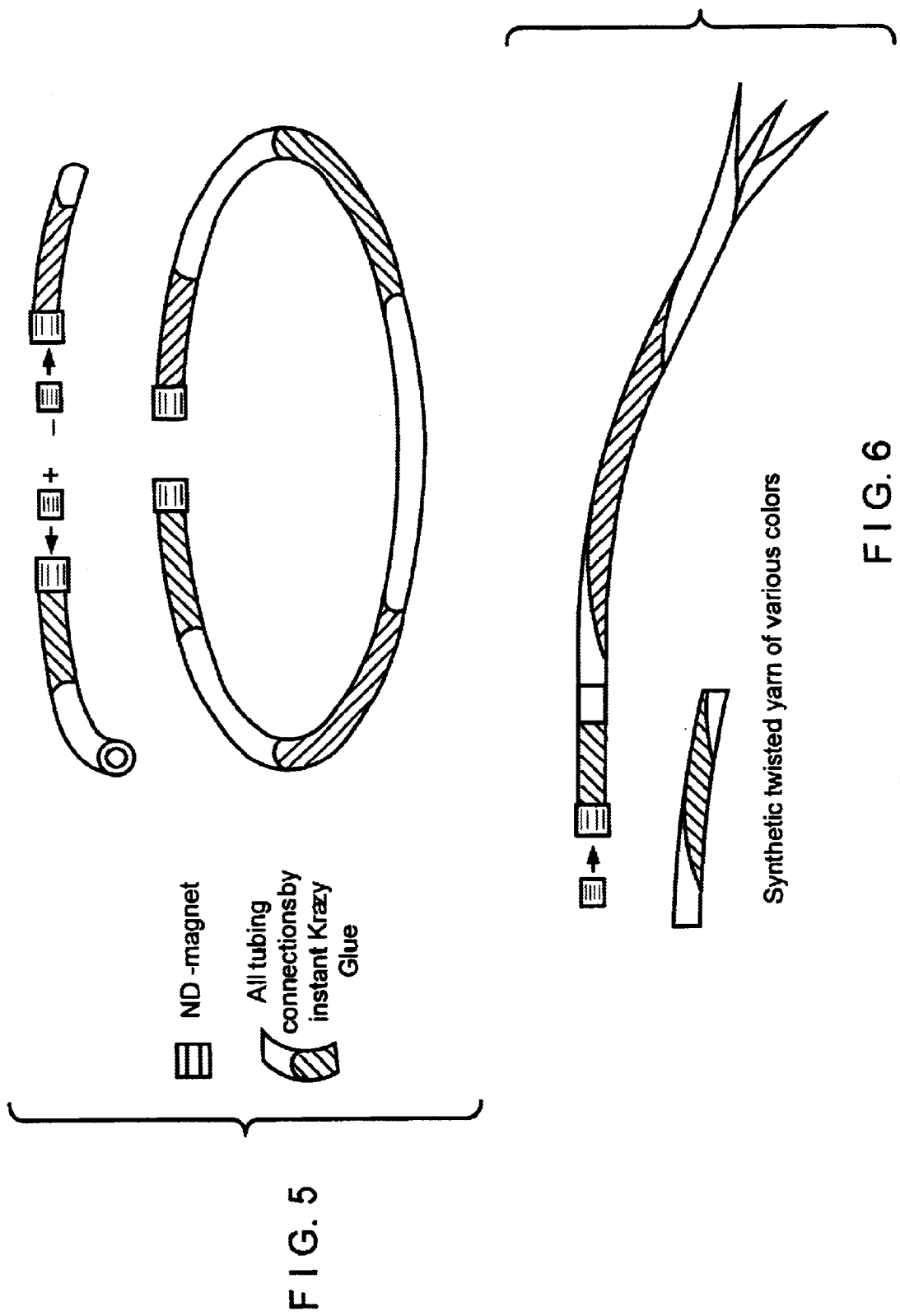

MAGNETIC KEY CHAIN

RELATED CASE

This application claims priority to Provisional Application No. 60/292140, filed May 18, 2001, entitled MAGNETIC KEY CHAIN, naming as inventors Jonathan J. Kaufman and Gocha Chkadua.

BACKGROUND OF THE INVENTION

The invention pertains to apparatus for improving the utility of key chains.

A variety of key chains have been commonly utilized. These have included the standard key ring attached to a "token", such as a plastic or metal piece in some shape. Often the piece is decorated with a particular icon, such as a flag or other symbol. In other cases, the piece may include a hook, for attaching, for example, to a belt loop. While decorative and somewhat functional, key chains have not been heretofore designed for maximum utility.

BRIEF STATEMENT OF THE INVENTION

It is accordingly an object of the invention to provide a key chain apparatus that is more useful than presently available.

Another object is to meet the above object, such that key chains can be more widely utilized.

A further object is to provide magnetic jewelry.

Another object is to provide magnetic therapy through use of the key chain and jewelry.

Briefly stated, the invention in its presently preferred form achieves the foregoing objects by construction of a magnetic key chain. The magnetic key chain is comprised of a rubber tube two inches in length. The outside diameter of the rubber tube is 0.250 inch, and the inside diameter is 0.050 inch. Inserted into one end of the rubber tube is a neodymium cylindrical magnet having a diameter of 0.250 inch and a length of 0.250 inch, in such a way so that the end of the magnet is flush with the end of the tube. In the presently preferred embodiment the diameter of the magnet is large enough to stretch the tube sufficiently so that the magnet is held firmly inside the tube, without the need for any glue or adhesive. At the other end of the tube, a metal plug or hook is inserted. The metal plug is also cylindrical; about half of it is inside the tube (this part has a diameter about the same as the magnet's), and about half of it projects out from the tube (this part has a slightly larger diameter, about equal to the external diameter of the tube when it is stretched by the insertion of the metal plug. On the half that projects out from the tube there is a hole, through which is attached a metal ring. The metal ring is used for attaching keys. As described, the presently preferred embodiment is ideal for keeping one's keys in a pocket or a pocketbook or backpack or other bag. It is also ideal for attaching to the inside surface of the front door of a home, or any other metal surface that is able to be attracted by magnets (i.e., a "magnetic" material). The key chain can even be "thrown" at a door, and it will "stick." It should be appreciated that in many cities, local fire codes require doors to be covered with steel, an ideal magnetic surface.

BRIEF DESCRIPTION OF THE DRAWINGS

The invention will be described in detail for a presently preferred embodiment, in conjunction with the accompanying drawings, in which:

FIG. 5 is a schematic diagram showing an alternative embodiment of the invention.

FIG. 6 is a schematic diagram showing an alternative embodiment of the invention.

DETAILED DESCRIPTION OF THE INVENTION

The invention will be described in detail for a presently preferred embodiment, in conjunction with the accompanying drawings.

The invention is shown in FIG. 1 through FIG. 4 in application to interconnected components for constructing apparatus used in the invention.

Figure 1:
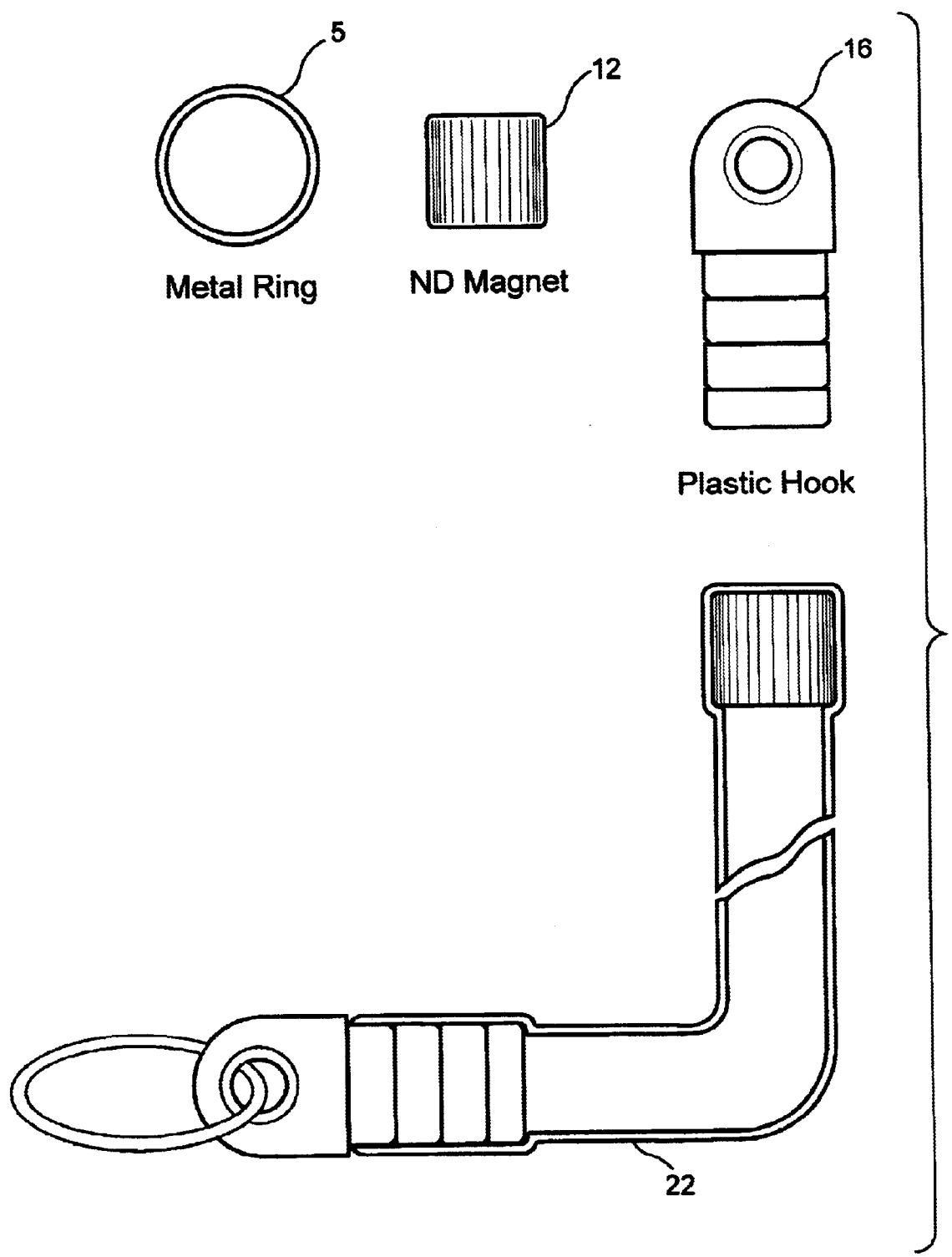
FIG. 1 is a schematic diagram showing an embodiment of the magnetic key chain.
Figure 2:
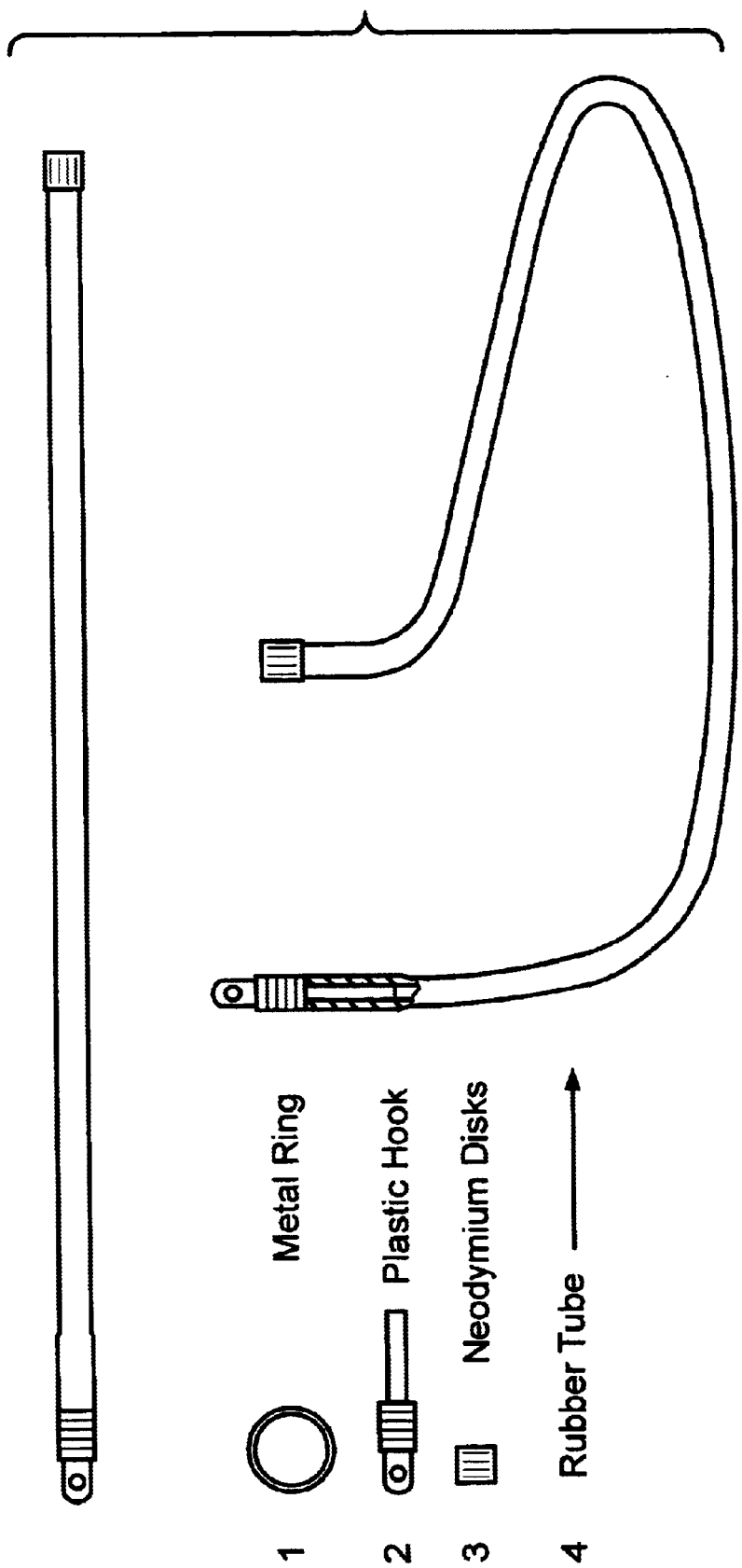
FIG. 2 is a schematic diagram showing another embodiment of the magnetic key chain.
Figure 3:
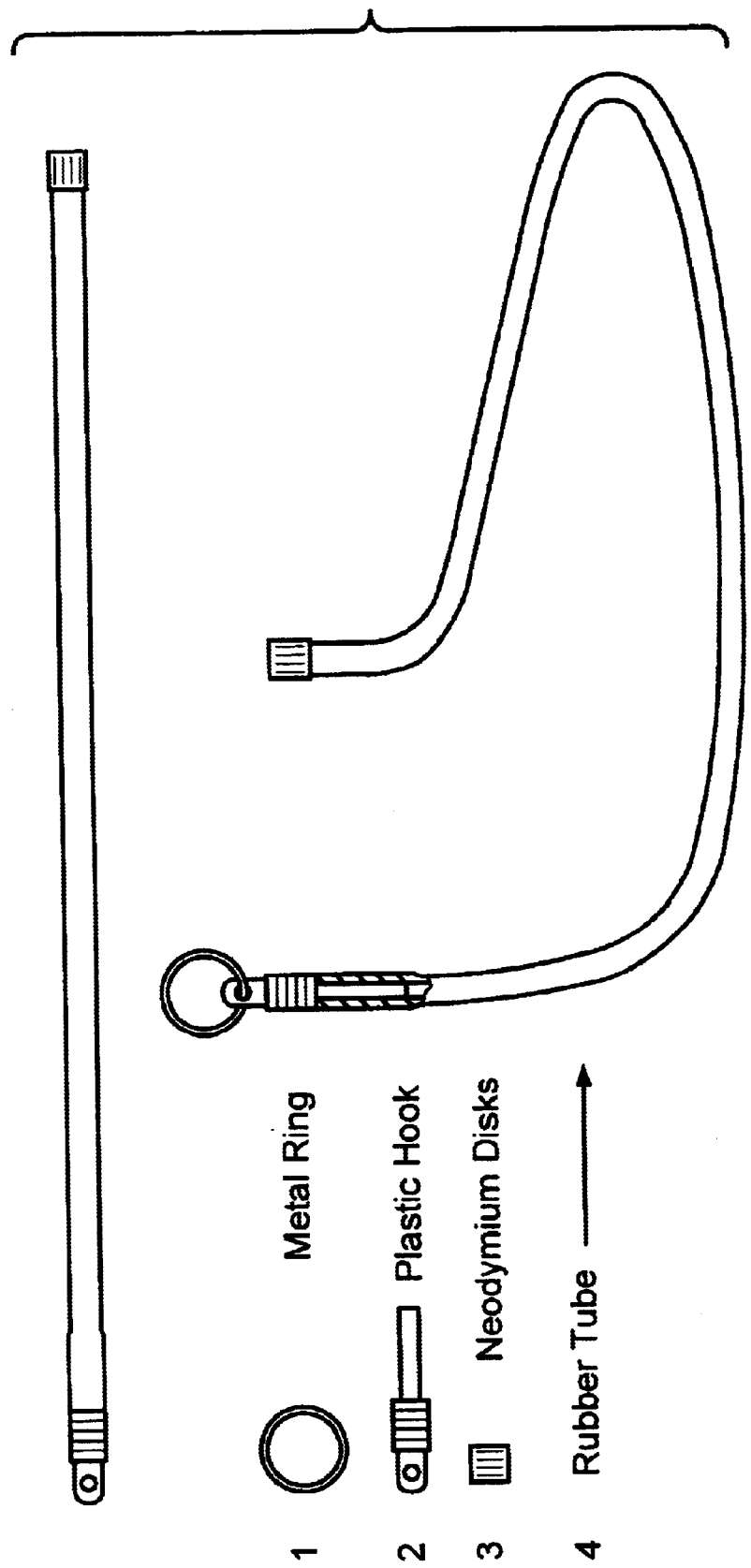
FIG. 3 is a schematic diagram showing another view of the magnetic key chain.
Figure 4:
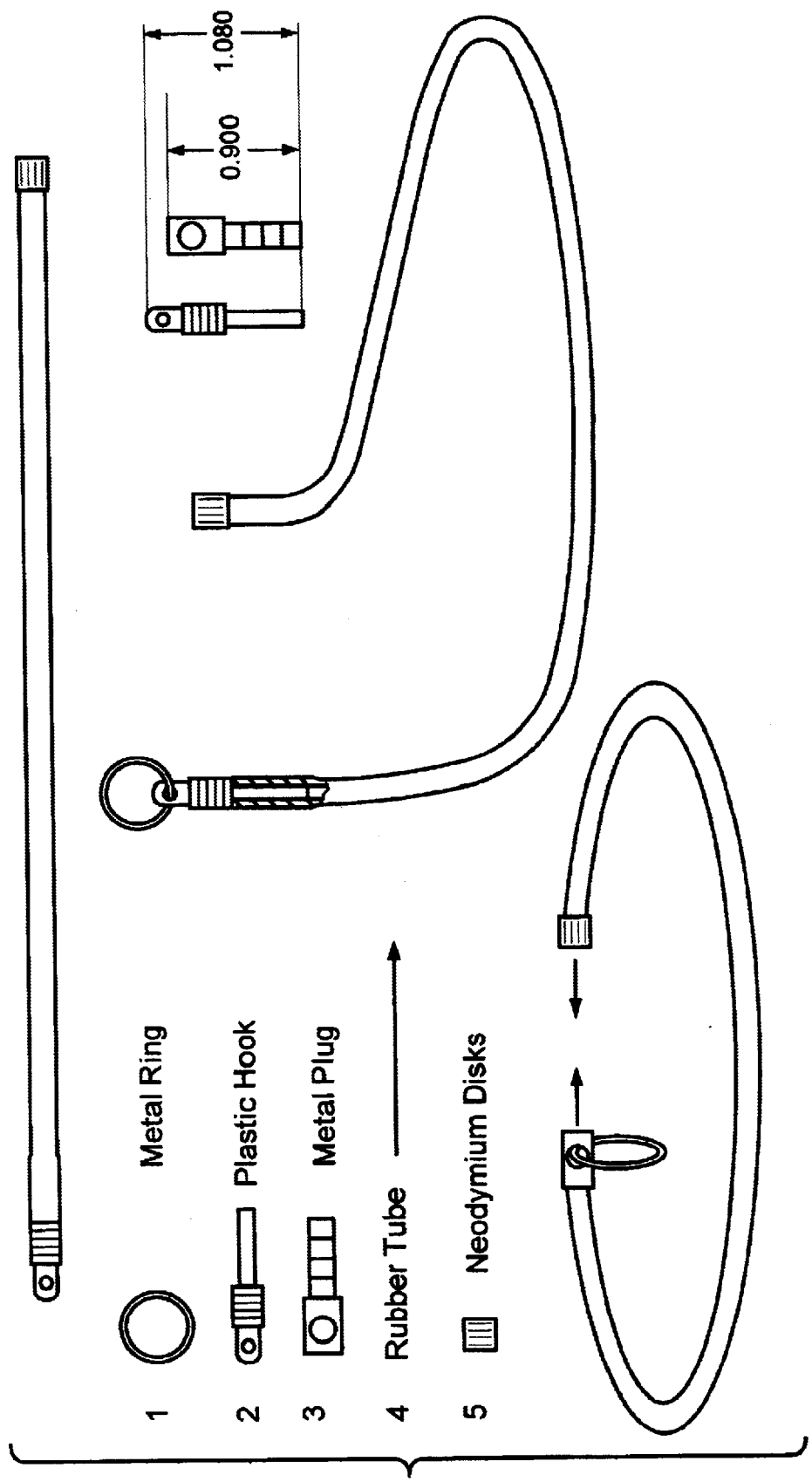
FIG. 4 is a schematic diagram showing an embodiment of the invention.

In FIG. 1, a magnetic key chain is shown to consist of a metal ring 5, a magnet 12, a hook 16, and a rubber tube 22. The magnetic key chain in a currently preferred embodiment is comprised of a rubber tube two inches in length. The outside diameter of the rubber tube is 0.250 inch, and the inside diameter is 0.050 inch. Inserted into one end of the rubber tube is a neodymium cylindrical magnet having a diameter of 0.250 inch and a length of 0.250 inch, in such a way so that the end of the magnet is flush with the end of the tube. In the presently preferred embodiment the diameter of the magnet is large enough to stretch the tube sufficiently so that the magnet is held firmly inside the tube, without the need for any glue or adhesive. At the other end of the tube, a hook is inserted. The hook is also cylindrical; about half of it is inside the tube (this part has a diameter about the same as the magnet's), and about half of it projects out from the tube (this part has a slightly larger diameter, about equal to the external diameter of the tube when it is stretched by the insertion of the metal plug. On the half that projects out from the tube there is a hole, through which is attached a metal ring. The metal ring is used for attaching keys. As described, the presently preferred embodiment is ideal for keeping one's keys in a pocket or a pocketbook or backpack or other bag. It is also ideal for attaching to the front door of a home, or any other metal surface that is able to be attracted by magnets (i.e., a "magnetic" material). The key chain can even be "thrown" at a door, and it will "stick." It should be appreciated that in many cities, local fire codes require doors to be covered with steel, an ideal magnetic surface.

FIGS. 1, 2, 3 and 4 are drawings of a presently preferred and several alternative embodiments of the invention. The above and following disclosure may best be understood with reference to these drawings. There are a number of alternative embodiments of the invention. Such alternative embodiments includes the use of either a metal plug or hook, or a plastic one, or any material suitable for attaching inside the tube and capable of being attached to the metal ring. The shape and features of the plug are the most important aspects (namely that it may be inserted into an end of the flexible tube, and that a ring may be inserted through it); the choice will often be dictated by ease of fabrication and costs. In an alternative embodiment, the hook does not protrude from the tube, but a hole in the hook is aligned with a hole in the tube, through which a ring may be attached. The ring is most often metal, but it should be understood that any material capable of holding keys and attaching to the hook may be used. Additional alternative embodiments of the magnetic key chain are realized through differences in the length of the flexible tube. The shortest practical length is about one inch (1"), while the longest can be about thirty inches (30"). Having lengths longer than one inch allows the key chain to be attached to not only a magnetic surface (like a door) but to also be worn on a person's body. For example, in an alternative embodiment of the invention, the rubber tube is 8.5" in length, and the hook is composed of a metal (magnetic) material. In this alternative embodiment, the key chain is wrapped around one's wrist, and the magnet at one end of the tube attracts (attaches to) the metal hook at the other end of the tube, thus forming a closed loop (like a bracelet with a magnetic clasp). In this way, one's keys are always close at hand, never having to search to find them, again a useful feature, especially in cities and at night. As a further benefit of the invention, the magnet is positioned so as to expose the wrist to a magnetic field. This magnetic field is useful for treating carpal tunnel syndrome, and in this alternative embodiment, the magnet is positioned at the underside of the wrist ("the palm side"), where the hand and wrist meet. The magnet may also be periodically rotated around the wrist, as this intermittent exposure has also been found to enhance the therapeutic action of the magnetic field. The magnetic key chain may be worn at different locations on the body, besides the wrist. For example, it can be worn around or near the elbow. For this it may be useful to use a slightly longer length of tube, say 10". Besides serving also as a useful position for retaining keys, being out of the way but accessible, the magnetic key chain in this position has the capability to treat "tennis elbow," or tendinitis at the elbow. The magnetic key chain may be worn around the neck as well. In this alternative embodiment lengths from about 16" to about 30" are best adapted. By using a length where the magnet sits around mid chest, therapeutic benefits related to reducing the risk of heart disease and heart attack may be realized. In general, a wide range of therapeutic benefits may be realized by wearing the magnetic key chain at a variety of locations on the body. Thus it should be understood that therapeutic treatment may be realized by the method comprising the step of placing the magnetic key chain around an anatomical site, whereby to expose the anatomical site to a magnetic field associated with the magnet or magnets in the magnetic key chain. It should be appreciated that the magnetic key chain is placed around the site and remains there owing to the magnetic attraction between the magnet at one end of the tube and the magnetic material at the other end.

A number of variations, as noted, can be understood to be in the scope of the present invention. These include (i) multiple colors of tubing, including on the same magnetic key ring; (ii) small colored plastic rings for finishing purposes, for example between the collar of the plastic hook and the flexible tube; (iii) additional metal key ring (to which the keys are actually attached) to attach to a metal ring that is itself attached to the plastic or metal hook; (iv) a special hook which is attached to the metal ring of the magnetic key chain, that is easily detachable to allow the keys to be removed; (v) a variety of different magnets, not necessarily neodymium, that can be used, as long as they have sufficient "strength," and including a variety of coatings, such as with nickel plating; (vi) extra magnets placed inside the flexible tube at various locations, mainly for purposes of providing for magnetic therapy on the body; (vi) magnets which are "poled" or magnetized not only along its cylindrical axis, but also so that the "North" and "South" poles are azimuthal; (vii) magnetic therapy associated with the magnet key chain for the purposes of reducing pain and inflammation, increasing blood flow, and other therapeutic benefits; and (viii) multiple lengths of tubing within the same magnetic key chain, having the same or different colors, and attached to each other through the use of either magnets or magnetic material placed inside the tubes.

It should also be appreciated that while a number of sizes have been given for presently preferred embodiments of the invention, any size useful in the context of a flexible tube containing at least one magnet at one end of the tube and a hook and metal ring at the other end of the tube should be considered to be within the scope of the present invention. Thus, tubes with smaller and larger diameters (both inner and outer), longer and wider magnets and hooks, and different shaped hooks can all be considered to be within the scope of the present invention.

It should also be understood that the present invention includes not only key chains but the use of the flexible tube with magnets as jewelry, i.e., an item of magnetic jewelry. In one such embodiment of the invention, and with reference to FIG. 5, a wrist bracelet is formed with a flexible tube 7" in length and two neodymium magnets; one of the magnets is inserted into one end of the tube, and the other magnet is inserted into the other end of the tube. In this way, the tube may be wrapped around the wrist, and the magnets brought into contact to form a bracelet. All of the variations and embodiments discussed herein regarding the magnetic key chain apply also to the magnetic jewelry. Thus, the magnetic jewelry can be understood to be used anywhere on a living body, including around the wrist, around the arm, fingers, legs, ankles and neck. For the neck, the tube length can be such that it hangs down at various lengths, including in the style of a "choker." As disclosed above, multiple colors and multiple pieces of tubing can be utilized, including small "sleeves" for color accents. The magnetic jewelry can also be understood to confer similar medical and therapeutic benefits as for the embodiments of the magnetic key chain, and thus must be placed adjacent to the anatomical site to be treated. Multiple colors of tubing can be connected together in several ways. The easiest is to use a glue on each end of the tubes so that they attach to one another. In the present invention, "Krazy Glue" has been found to be ideal; however any glue which securely attaches the tubes to one another is within the scope of the present invention. Alternatively, the tubes can be kept flush with one another by having them both slip over a magnet or other cylindrical piece (e.g., the hook). This can be ideal with very short lengths of tube for example, with a 1.5 inch magnetic key chain. Although the use of 2 magnets is preferred for the bracelets and other jewelry disclosed herein, in order to most firmly secure it around the body, it is also possible to use only one magnet inserted at one end of the tube and a magnetic material inserted at the other end. Additional magnets within the tube (more than just at the ends) can also be used to provide additional therapeutic benefits. It of course should be understood that the magnets at the ends of tube are oriented so that they attract one another (North pole to South pole).

In general, a wide range of therapeutic benefits may be realized by wearing the magnetic jewelry at a variety of locations on the body. Thus it should be understood that therapeutic treatment may be realized by the method comprising the step of placing the magnetic jewelry around an anatomical site, whereby to expose the anatomical site to a magnetic field associated with the magnet or magnets in the magnetic jewelry. It should be appreciated that the magnetic jewelry is placed around the site and remains there owing to the magnetic attraction between the magnet at one end of the tube and the magnetic material or another magnet at the other end.

In addition, an add-on feature of the invention includes magnetic darts. As shown in FIG. 6, the magnetic darts have a short piece of flexible tube (a first tube), with a magnet inserted as with the magnetic key chain. In the presently preferred embodiment, the length of tubing is about ½ inch long. Another length of tube (a second tube), used as a sleeve, covers the end of a piece of fabric (in this preferred embodiment the fabric is four twisted strands of wool), whose overall length is about 10 inches long. The sleeve is placed (attached) adjacent to the first tube and magnet. The wool can be of any of a number of colors, and may be multi-stranded or single-stranded. Other materials can be used as well, such as (but not limited to) velvet, leather or cotton. The wool is attached to the tube using glue; in this embodiment Krazy Glue is used. It should be appreciated that the fabric can be attached to either the first tube, the magnet, the second tube (which itself is attached to the first tube), or all three. In this embodiment, the second tube is glued to the first tube. The darts can be magnetically attached to the magnetic key chain or to the jewelry, as a decorative addition. They can also serve as toys on their own, for example to be thrown at a magnetic material. The darts can be adorned with various ornaments or decorative pieces. In one alternative embodiment, small "eyes" are attached to the tube, near the end with the magnet.

Finally, it should be understood that any flexible tubing material may be used in the various embodiments of the invention, although the presently preferred material is latex rubber.

While several embodiments of the present invention have been disclosed hereinabove, it is to be understood that these embodiments are given by example only and not in a limiting sense. Those skilled in the art may make various modifications and additions to the preferred embodiments chosen to illustrate the invention without departing from the spirit and scope of the present contribution to the art. Accordingly, it is to be realized that the patent protection sought and to be afforded hereby shall be deemed to extend to the subject matter claimed and all equivalence thereof fairly within the scope of the invention.

It will be seen that the described invention meets all stated objectives as to providing a extremely useful key chain, with specific advantages that include but are not limited to the following:

(1) Ability to attach the key chain to any magnetic material, like a front door of a home, or a refrigerator;
(2) Ability to wear very simple but decorative jewelry;
(3) Ability to therapeutically treat various ailments and to provide generally health benefits to the individual using the magnetic key chain or wearing the magnetic jewelry.

What is claimed is:

1. A method of therapeutically treating an anatomical site in a living body, using a magnetic key chain, said magnetic key chain including a flexible tube having a first end and a second end, a magnet attached to said first end of said tube, a hook attached to said second end of said tube, and a ring attached to said hook, said method comprising the step of placing said magnetic key chain around said anatomical site, whereby to expose said anatomical site to a magnetic field associated with said magnet in said magnetic key chain.

2. The method of claim 1, wherein said anatomical site is a wrist.

3. The method of claim 1, wherein said anatomical site is an elbow.

4. The method of claim 1, wherein said anatomical site is a heart.

5. The method of claim 1, wherein said magnet is inserted into said first end of said tube and engaged in an interference fit with said first end of said tube, a first end of said magnet disposed within said tube and a second end of said magnet flush with the first end of said tube.

6. The method of claim 1 wherein said hook is inserted into said second end of said tube, said hook having a first portion having a first diameter sized to be received within said second end of said tube and a second portion having a second diameter greater than said first diameter and about equal to an outer diameter of said second end of said tube following insertion of said hook into said second end of said tube, said hook including an aperture proximate a first end of said hook.

7. A magnetic key chain, said magnetic key chain comprising a ring, a magnet, a hook and a flexible tube having a first end and a second end, wherein said magnet being attached to said first end of said tube and said hook being attached to said second end of said tube, and wherein said ring being attached to said hook.

8. The magnetic key chain according to claim 7, wherein said magnet is a neodymium magnet.

9. The magnetic key chain of claim 7, wherein said flexible tube is rubber.

10. The magnetic key chain of claim 7 wherein said magnet is inserted into said first end of said tube.

11. The magnetic key chain of claim 10 wherein a first end of said magnet is disposed within said tube and a second end of said magnet is flush with the end of said tube.

12. The magnetic key chain of claim 10 wherein said magnet is engaged in an interference fit with said first end of said tube.

13. The magnetic key chain of claim 7 wherein said hook is inserted into said second end of said tube.

14. The magnetic key chain of claim 7 wherein said hook includes an aperture proximate a first end of said hook, and said ring extends through said aperture.

15. The magnetic key chain of claim 14 wherein said second diameter is about equal to an outer diameter of said second end of said tube following insertion of said hook into said second end of said tube.

16. The magnetic key chain of claim 7 wherein said aperture is aligned with a corresponding aperture in said tube and said ring extends through said aperture in said tube.

17. The magnetic key chain of claim 7 wherein said hook has a first portion having a first diameter sized to be received within said second end of said tube and a second portion having a second diameter greater than said first diameter.

18. The magnetic key chain of claim 7, further comprising a second magnet disposed within said tube.

19. The magnetic key chain of claim 7, further comprising a second tube and one of a second magnet and a magnetic material coupled to said second tube and to said first magnet of said first tube.

20. A magnetic key chain, comprising:
a flexible tube having a first end and a second end;
a magnet inserted into said first end of said tube and engaged in an interference fit with said first end of said tube, a first end of said magnet disposed within said tube and a second end of said magnet flush with the first end of said tube;

a hook inserted into said second end of said tube, said hook having a first portion having a first diameter sized to be received within said second end of said tube and a second portion having a second diameter greater than said first diameter and about equal to an outer diameter of said second end of said tube following insertion of said hook into said second end of said tube, said hook including an aperture proximate a first end of said hook; and, a ring extending through said aperture in said hook.